United States Patent [19]
Lane et al.

[11] Patent Number: 6,103,695
[45] Date of Patent: Aug. 15, 2000

[54] METHOD OF PRODUCING PLEURODESIS

[75] Inventors: Kirk B. Lane; Richard Light, both of Brentwood; Jeffrey M. Davidson, Nashville, all of Tenn.

[73] Assignee: Vanderbilt University, Nashville, Tenn.

[21] Appl. No.: 09/416,869

[22] Filed: Oct. 13, 1999

Related U.S. Application Data

[60] Provisional application No. 60/104,167, Oct. 14, 1998.

[51] Int. Cl.$^7$ .................................................. A61K 38/00
[52] U.S. Cl. ............................................................ 514/12
[58] Field of Search ................................................ 514/12

[56] References Cited

U.S. PATENT DOCUMENTS

| | | | |
|---|---|---|---|
| 5,312,331 | 5/1994 | Knoepfler | 604/49 |
| 5,478,837 | 12/1995 | Rodgers et al. | 514/297 |
| 5,597,578 | 1/1997 | Brown et al. | 424/422 |

OTHER PUBLICATIONS

Light et al., "Pleural sclerosis for the treatment of pneumothorax and pleural effusion", *Lung* 1997; 175:213–223.

Light et al., "Intrapleural tetracycline for the prevention of recurrent spontaneous pneumothrax", *JAMA* 1990; 264:2224–2230.

Vargas et al., "Effectiveness of bleomycin in comparison to tetracycline as pleural sclerosing agent in rabbits", *Chest* 1993; 104:1582–1584.

Xie et al., "Serial observations after high dose talc slurry in the rabbit model for pleurodesis", *Lung* 1998; 176:299–307.

Wu et al., "Doxycycline Pleurodesis in rabbits. Comparison of results with and without chest tube." *Chest* 1998; 114:563–568.

Sahn et al., "The effect of common sclerosing agents on the rabbits pleural space", *Am Rev Respir Dis* 1981; 124:65–67.

Vargas et al., "Acute and chronic pleural changes after the intrapleural instillation of mitoxantrone in rabbits", *Lung* 1998; 176:227–236.

Kennedy et al., "Talc slurry pleurodesis, Pleural fluid and histologic analysis", *Chest* 1995; 107:1707–1712.

Light et al., "Comparison of the effectiveness of tetracycline and minocycline as pleural sclerosing agents–In rabbits", *Chest* 1994; 106:577–582.

Sassoon et al., "Temporal evolution of pleural fibrosis induced by intrapleral minocycline injection", *Am J. Respir Crit Care Med* 1995; 151:791–794.

Xie et al., "Systemic corticosteroids decrease the effectiveness of talc pleurodesis", *Am J. Respir Crit Care Med* 1998; 157:1441–1444.

Cheng et al., "The effects of intrapleural polyclonal anti–tumor necrosis factor alpha (TNFα) Fab fragments on pleurodesis in rabbits", *Lung* 2000; 178:000–000.

Teixeira, et al., "The effect of corticosteroids on pleurodesis induced with doxycycline in rabbits", *Chest* 1997; 112:137S.

Walker–Renard, et al., "Chemical pleurodesis for malignant pleural effusions", *Ann Intern Med* 1994; 120:56–64.

Milanez–Campos et al., "Respiratory failure due to insufflated talc", *Lancet* 1997; 349:251–252.

*Primary Examiner*—Raymond Henley, III
*Attorney, Agent, or Firm*—Needle & Rosenberg, P.C.

[57] ABSTRACT

The present invention provides a method of producing a pleurodesis in a mammal, comprising introducing a therapeutically effective dose of a pharmaceutical composition comprising TGFβ into the pleural cavity.

14 Claims, 9 Drawing Sheets

METHOD OF PRODUCING PLEURODESIS

This application claims priority to U.S. provisional application Ser. No. 60/104,167, filed Oct. 14, 1998, and the No. 60/104,167 application is herein incorporated by this reference in its entirety.

BACKGROUND OF THE INVENTION

There are over a million cases of pleural effusion due to malignancies and pneumothorax each year in the United States. While all of these are not candidates for pleurodesis, the percentage that receive pleura sclerosing therapy is high. "Pleurodesis" is the fusion of the visceral and parietal pleura resulting from the therapeutic injection of a substance into the pleural cavity. The injected substance causes fibrosis between the visceral and parietal pleura and obliteration of the potential space between the two. Current treatment involves the introduction of a non-specific irritant into the pleural space. This treatment is painful and not always satisfactory.

The initial event in the production of a pleurodesis is an injury to the pleura. An acute exudative pleural effusion develops within 12 hours of the installation of essentially all of the agents that are presently used for pleurodesis including talc (9), tetracycline derivatives (10), quinacrine (11), mitoxantrone (12) and bleomycin (4). The pleural fluid that accumulates after the intrapleural injection of these agents is initially characterized by a relatively high protein, LDH and neutrophil count. However, injury to the pleura, as evidenced by the production of an acute exudative pleural effusion, is not sufficient to induce a pleurodesis because many agents when injected into the pleural cavity produce an acute exudative effusion but do not produce a pleurodesis (11).

The response by the pleura to an injury is a complex and poorly understood multifactorial process which can result either in the development of fibrosis with the obliteration of the pleural space or in restoration of the pleura to its normal state. The histological patterns of pleural fibrosis associated with the administration of nitoxantrone (12), talc (9, 13) or tetracycline derivatives (14, 15) are different. The mechanisms by which pleurodesis follows the intrapleural administration of tetracycline derivatives and talc also appear to be different. The pleurodesis that follows talc can be blocked if corticosteroids are administered systemically (16) or by the administration of tumor necrosis factor alpha blocking antibodies (17). In contrast, the pleurodesis that follows doxycycline is not blocked by either of these agents (18).

The agents most commonly used for the production of a pleurodesis are the tetracycline derivatives, talc in a slurry, and bleomycin (1). None of these compounds is ideal. The injection of a tetracycline compound is at times very painful (2). The injection of talc leads to the development of the acute respiratory distress syndrome in a small percentage of recipients, and this syndrome is at times fatal (3). The injection of bleomycin does not induce pleurodesis in animals with a normal pleura (4) and the bleomycin itself is very expensive, costing more than $1000 per injection. As talc and other commonly used agents produce pleurodesis by inducing injury to the pleura which leads to inflammation and fibrosis (32), pain and fever are common side effects (29).

Because injecting talc to create a pleurodesis is associated with mortality, because injecting tetracycline derivatives is painful, and because injecting bleomycin is very expensive and relatively ineffective, there exists a great need to find a safe, well-tolerated and inexpensive method for creating a pleurodesis.

The present invention meets this need and overcomes the previous limitations and shortcomings in the art by providing a safe, well-tolerated, inexpensive effective method for creating a pleurodesis by using TGFβ2. Transforming growth factor beta-2, TGFβ2, a specific fibrogenic agent, is effective at causing pleurodesis. TGFβ$_2$ produces excellent pleurodesis in rabbit and sheep models of pleurodesis with less pleural inflammation than currently used agents (28). The pleura of sheep closely resembles the human pleura. Like humans, sheep have a thick pleura which receives its blood supply from the systemic circulation (28). Hence sheep are an accepted model for the study of pleural fluid dynamics (29, 30).

SUMMARY OF THE INVENTION

The present invention provides a method of producing a pleurodesis in a mammal, comprising introducing a therapeutically effective dose of a pharmaceutical composition comprising TGFβ into the pleural cavity, whereby pleurodesis is produced.

DETAILED DESCRIPTION OF THE INVENTION

Figure 1:
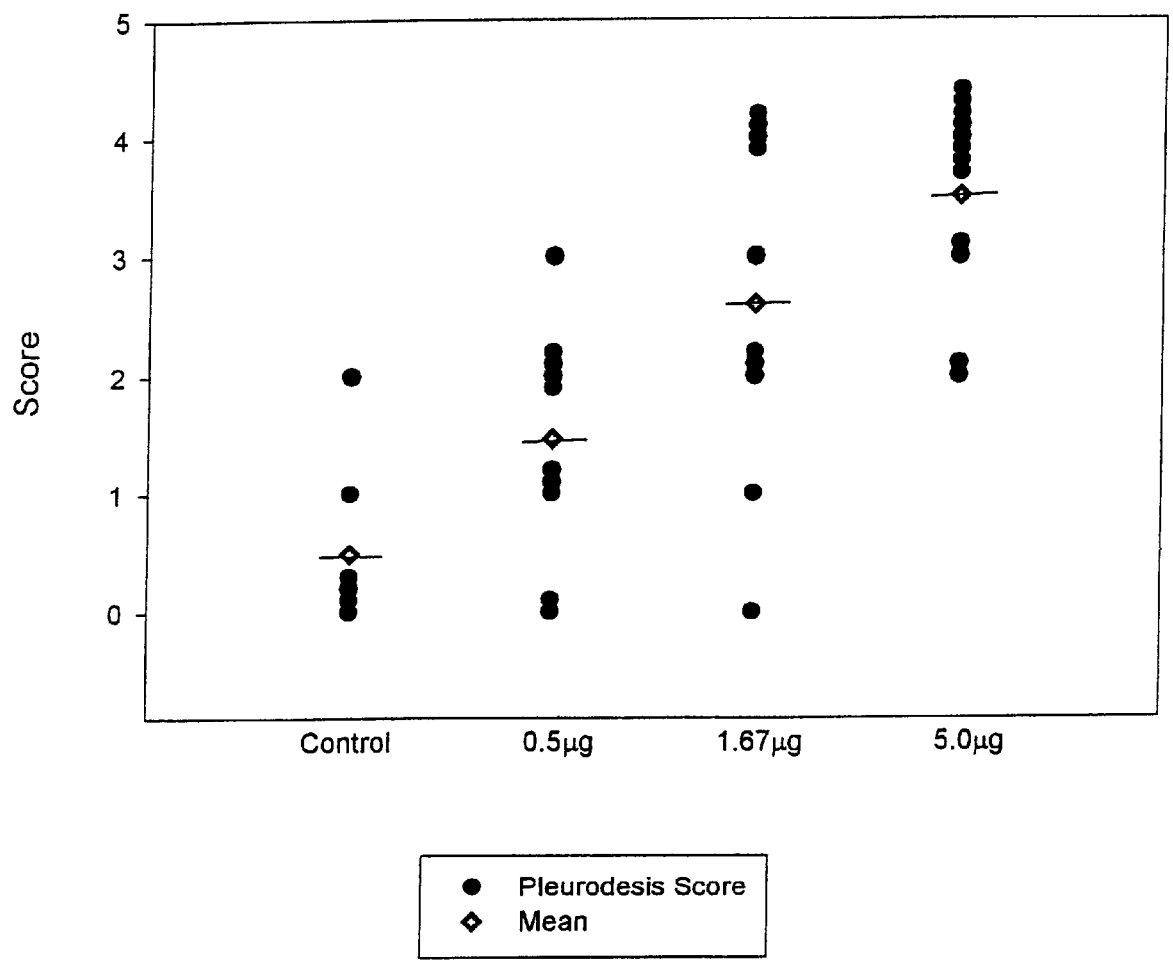
FIG. 1. Degree of pleurodesis after the intrapleural injection of the buffer and varying doses of TGF $β_2$. Note the nice dose response curve.

As used herein, "a," "an" or "the" may mean one or more. For example, "a", cell may mean one cell or more than one cell.

The present invention is based on the unexpected and surprising discovery that a method of producing a pleurodesis in mammals by injecting TGFβ is safer, relatively less expensive and less painful than currently used methods of treatment. The present invention provides a method of producing a pleurodesis in a mammal, comprising introducing a therapeutically effective dose of a pharmaceutical composition comprising TGFβ into the pleural cavity, whereby pleurodesis is produced. Also provided is a method of producing a pleurodesis in a mammal, comprising a) introducing a catheter into the pleural cavity, b) evacuating air and/or fluid from the pleural cavity and c) delivering a therapeutically effective dose of a pharmaceutical composition comprising TGFβ into the pleural cavity, whereby pleurodesis is produced. "TGFβ" as used herein includes $TGF\beta_1$, $TGF\beta_2$ and $TGF\beta_3$.

To create a pleurodesis, the physician properly positions the patient to allow the catheter to enter the pleural cavity where there is air, in the case of pneumothorax, or in an area of dependent fluid, in the case of pleural effusion. The patient's skin is prepared and draped in the usual sterile manner. After locating the intercostal space through which the catheter will pass, a local anesthetic is injected into the tissues of the chest wall. After local anesthesia has been achieved, the needle and catheter are passed through the chest wall, penetrating the parietal pleura and entering the pleural cavity. After the catheter is in the pleural cavity, air is removed to re-expand the lung in the case of pneumothorax or fluid is withdrawn in the case of pleural effusion. Following the evacuation of either air or fluid, a therapeutically effective dose of TGFβ is injected into the pleural cavity and left in place for at least 2 hours. Once the pleural effusion resolves or reaches a minimal level, the catheter may be withdrawn and a bandage placed over the penetration site. Numerous additions or modifications to this procedure can be made by the skilled physician and still be in accordance with the invention. For example, a physician may choose to enter the pleural cavity with a needle and insert no catheter into the pleural cavity.

When used, the catheter may be left in place within the pleural cavity to withdraw fluid or continually monitor the composition of the pleural fluid to determine the changes in the fluid caused by the injection of the TGFβ. By this method, the fluid can be studied on a continuing basis to determine its chemical and cytologic composition over time. For example, pleural fluid LDH, pleural fluid protein and glucose, WBC counts and differential can be studied as described in the Examples. Moreover, the cells in the pleural fluid can be examined for signs of malignancy.

The method of producing a pleurodesis comprises injecting a pharmaceutically acceptable composition comprising TGFβ and a physiologically acceptable buffer. One embodiment of the present invention is a pharmaceutically acceptable composition comprising TGFβ present in a dose of 0.125 $\mu$g/Kg to 1.0 $\mu$g/Kg body weight and phosphate buffered saline.

A preferred embodiment of the present invention is a pharmaceutically acceptable composition comprising $TGF\beta_2$, sodium phosphate, sodium chloride, propylene glycol and polyethylene glycol 400, in which the $TGF\beta_2$ is present in a dose of 0.125 $\mu$g/Kg to 1.0 $\mu$g/Kg body weight. The concentration of sodium phosphate is 20 mM; the concentration of sodium chloride is 130 mM; the concentration of propylene glycol is 15% (w/w); and the concentration of polyethylene glycol 400 is 20% (w/w).

Moreover, it would be known to a person of ordinary skill in the art that the concentration ranges of the buffers may be varied. Thus, the concentration of sodium phosphate may be 2 mM to 100 mM; the concentration of sodium chloride may be 10 mM to 200 mM; the concentration of propylene glycol may be 5% to 25% (w/w); and the concentration of polyethylene glycol 400 may be 5% to 30% (w/w).

The present invention is more particularly described in the following examples which are intended as illustrative only since numerous modifications and variations therein will be apparent to those skilled in the art.

EXAMPLE 1
Production of Pleurodesis in a Rabbit Model

New Zealand white rabbits with a weight between 1.5 to 2.5 Kg were used. The initial studies were designed to determine the lowest dose of TGF β2 that will produce a pleurodesis (mean pleurodesis score>3.0) in rabbits 14 days after the injection of the growth factor in either a PEG buffer solution or a slow release pleuronic gel. The following five groups, for each delivery system, each with 10 rabbits, were studied. The total volume of the injectate for each rabbit was 2 mL.

A. Vehicle alone.
B. 5$\mu$g TGF β2 in 2 mL vehicle
C. 1.67 TGF β2 in 2 mL vehicle
D. 0.5 TGF β2 in 2 mL vehicle
E. 0.167 TGF β2 in 2 mL vehicle A second set of experiments revealed pleural fluid findings and the histological findings after the intrapleural administration of the lowest effective dose of TGF β2 in the most appropriate vehicle. Rabbits are injected with the lowest effective dose of the TGF β2 and 10 rabbits are sacrificed at each of the following time intervals: 1 day, 2 days, 4 days, 7 days, 30 days and 60 days.

Prior to the administration of the growth factor, the rabbits were anesthetized with ketamine hydrochloride 36 mg/kg and xylazine hydrochloride 5 mg/kg intramuscularly. The thorax was prepared for aseptic surgery by shaving the right chest wall and then cleaning it with povidone-iodine or alcohol.

At the time of the intrapleural injection, all the rabbits received a chest tube on the right side. A 0.5 cm skin incision was made at a site which is approximately 4 cm anterior to the spine and 2 cm above the lower margin of the ribs. After the parietal pleura was reached by bluntly dissecting the muscles underlying the skin incision, a small hole was made in the parietal pleura with surgical forceps. This allows the right lung to collapse, thereby preventing damage to the lung when the catheter was placed. A 0.1 cm diameter soft plastic catheter was then inserted into the pleural space. In sequence, the muscles and tissues were sutured and the catheter was fixed to the chest wall. The proximal tip of the catheter was tunneled under the skin and drawn out through the skin posteriorly and superiorly between the low scapulae and was fixed to the skin with a silk suture.

The exterior end of the catheter was plugged with a self-sealing rubber plug. Air or liquid was aspirated from the pleural space by inserting a #18 needle through the self-sealing plug. After the surgery, the rabbits were closely monitored for clinical evidence of pain (vocalization, tachypnea, and restlessness) The left hemithorax received no injection and served as a control.

After all air was aspirated from the pleural space, the TGF β2 in a total volume of 2 ml was injected into the pleural space. The investigator was blinded as to which dose of TGF β2 the animal received. The accumulated pleural fluid was aspirated every 24 hours for at least 72 hours and until the amount of fluid which accumulated in the previous 24 hours was less than 5 ml. If the catheter appeared to be obstructed, attempts were made to restore its patency by injecting 0.1 ml saline. If the chest tube remained obstructed, streptokinase 0.1 ml was injected into the tube. After one hour, attempts were again made to aspirate the pleural fluid. When the chest tube was removed, the rabbits were lightly anesthetized with ketamine hydrochloride, 17 mg/kg, and xylazine hydrochloride 2.5 mg/kg.

Each time pleural fluid was aspirated, the initial 0.2 ml was discarded. The amount of fluid recovered at each aspiration and its gross appearance was recorded. The fluid was analyzed for cell count, differential, glucose and protein content via refractometer. The fluid was stored in citrated test tubes. Subsequently, the fluid was centrifuged at 5000 rpm for 12.5 minutes. The cells were preserved for future analysis. The fluid was frozen at −70 degrees centigrade. Subsequently these frozen samples are analyzed for the levels of LDH and the following cytokines: TGF $\beta$1, TGF $\beta$2, TNF, IL-1, IL-6, IL-8, and VEGF.

After 14 days the rabbits were sacrificed by the injection of 40 mg/kg pentobarbital solution into the marginal ear vein. Then the thorax was removed en bloc. Specimens of the kidney, liver and adrenal gland were placed in 10% formaldehyde. The thorax was then opened and the degree of gross adhesions was graded according to the following scheme.

0—Normal pleural space
1—1–3 small adhesions in the pleural space
2—3 scattered adhesions but lung easily separated from chest wall;
3—generalized scattered adhesions with areas where the lung can be separated from the chest wall only with difficulty;
4—complete obliteration of the pleural space by adhesions.

The effectiveness of the pleurodesis was assessed according to the following scheme:

1—Poor—Presence of one or more of the following:
Score 2 or less for adhesions
Hemothorax or effusion score of 3 or 4
Complete atelectasis.
2—Acceptable—Presence of the following:
Gross adhesion score of 3 or 4
Hemothorax or effusion score of 2 or less
None or partial atelectasis
3—Excellent—Presence of both the following:
Gross adhesion score of 4
No hemothorax, pleural effusion or atelectasis Objective measures of pleurodesis include fresh and formalin fixed tensiometry of the adhesions. The total adhesive index of the lung may be determined by measuring the force required to remove the treated lung from the chest wall.

At the time that the pleura was evaluated grossly, two samples of the intact chest wall plus the pleural tissue and lung approximately 3×3×3 cm were obtained. These two specimens were bisected half of each were placed in 10% formalin for at least one week. The other half were placed in 2% paraformaldehyde for one day and then maintained at 4 degrees centigrade until examined. For hemithoraces with no pleurodesis, the specimens of the chest wall and lung were obtained separately. These tissue samples preserved in formaldehyde were processed routinely and stained with hematoxylin and eosin (H&E) and Trichrome to assess the connective tissue content. The content was determined by quantitative morphometry of the area of fibrosis. The degree of microscopic inflammation and fibrosis was graded 0 (none), equivocal (1), mild (2), moderate (3) or marked (4) as previously described (1). The tissue sample preserved in paraformaldehyde is used for immuno-histochemistry so that the cytokeratin of the mesothelial layer can be evaluated.

The collected pleural fluid is subjected to the analysis for the presence of human TGF $\beta$2, TGF $\beta$1, rodent VEGF, rodent TNF$\alpha$, rodent IL- 1$\beta$, rodent IL-6, and IL-8 by commercially available immunoassay. The assay for human TGF $\beta$2 confirmed the presence of the delivered cytokine and allowed a determination of the persistence of the treatment molecule in the pleural space.

The initial assays are conducted with two standards, mouse and rabbit. The standard curve from these two sources are used to confirm the kits' ability to detect rabbit cytokines.

The IL-6, IL-8, and TNF$\alpha$ are assayed as markers of inflammation induction during the initial stages of pleurodesis. These assays are performed on cells obtained from the pleural fluid at the stated time points. The cells in the collected fluid are pelleted by low speed centrifugation and lysed with a commercial RNA isolation reagent (Tri-reagent, Trizol). RT was conducted using Pharmacia's first strand cDNA synthesis kit. The method of quantitation is that of Chang (24) briefly, mRNA is converted to cDNA by polyT primed reverse transcription. The ss cDNA is polyA tailed by polyA polymerase. An aliquot of the cDNA is then subjected to PCR utilizing a single polyT primer. The products are run on an agarose gel, transferred to a hybridization membrane and probed for the genes of interest. Probes representing constitutive message are also used in these blots to control for loading variations. To determine that the RT-PCR methodology is accurate, the TNF$\alpha$ findings are confirmed by the L929 cell assay (25). Finally, the cell type(s) responsible for the production of the mediators are investigated by in situ hybridization.

Mesothelial cells are capable of producing extracellular matrix proteins (26) and have been proposed to be pivotal in the repair of mesothelial injury (27). The up regulation of these messages, collagen and laminin were assayed by molecular means. If sufficient material is available northern blots are conducted to determine the amount of extracellular matrix mRNA present at the different sampling points. If the material is limiting ribonuclease protection assays or quantitative RT-PCR are used to follow the expression of these gene in response to TGF $\beta$2. Along with the extracellular matrix genes the tissues were assayed for the presence of mesothelial markers (cytokeratin) to confirm that the induction of extracellular matrix is occurring in the mesothelium or from infiltrating fibroblasts.

EXAMPLE 2

Production of Pleurodesis by and Dose Response to TGF$\beta$2 in a RABBIT MODEL

New Zealand white male rabbits weighing 1.5–2.5 kg were lightly anesthetized with ketamine hydrochloride, 35 mg/kg, plus xylazine hydrochloride, 5 mg/kg intramuscularly. The thorax was prepared for aseptic surgery by shaving the right chest wall and then sterilizing it with povidine-iodine and alcohol. The rabbit was placed in the lateral decubitus position. A 0.5 cm skin incision was made at a site which was approximately 4 cm anterior to the spine and 2 cm above the lower margin of the ribs. The parietal pleura was reached by bluntly dissecting the muscles underlying the skin incision. A small hole was made in the parietal pleura with the surgical forceps. This allowed the right lung to collapse, thereby preventing damage to the lung when the catheter was placed. A soft Silastic catheter (inside diameter $\frac{1}{32}$", outside diameter $\frac{1}{16}$", Dow Corning, Medland, Mich.)

was inserted into the pleural space. In sequence, the muscles and tissues were sutured and the catheter was fixed to the chest wall. The proximal tip of the catheter was tunneled under the skin and drawn out through the skin posteriorly and superiorly between the two scapulae and fixed to the skin with a silk suture.

The exterior end of the catheter was plugged using a stub adaptor with a Luer lock fitting (Cole Parmer, Vernon Hill, Ill.). A self-sealing injection site fitting with a Luer lock was then attached to the stub adaptor (Baxter Health Care Corporation, Deerfield, Ill.). Air or liquid could be aspirated from the pleural space by inserting a 18 gauge needle through the self-sealing plug. After the surgery, the rabbits were closely monitored for clinical evidence of pain (vocalization, tachypnea, and restlessness). The left hemithorax received no injection and served as a control. The chest tubes were left in place for 24 hours before any intrapleural injections were made.

The TGF used for these experiments was the $TGF\beta_2$ isoform (Genzyme Corporation, Framingham, Mass.). The $TGF\beta_2$ was a recombinant human $TGF\beta_2$ produced in Chinese hamster ovarian cells. The $TGF\beta_2$ was formulated in a vehicle consisting of 20 mM sodium phosphate, 130 mM sodium chloride, 15% (w/w)propylene glycol, 20% (w/w) polyethylene glycol 400, pH 7.2. The vehicle was prepared using USP/NF grade reagents in water for injection and sterile filtered through a 0.2 micron filter. The $TGF\beta_2$ concentration was determined by a sandwich enzyme-linked immunosorbent assay (ELISA) utilizing two monoclonal antibodies that cross react with both $TGF\beta_2$ and $TGF\beta_3$. The activity of the $TGF\beta_2$ was determined using a mink lung cell (Mv1Lu) antiproliferation assay, modified from the method described by Ogawa and Seyedin (40). The stability of $TGF\beta_2$ in the above vehicle had previously been demonstrated.

In the first experiment, 10 rabbits were included. Four rabbits each received a series of four intrapleural injections of the buffer, $TGF\beta_2$ 5 µg, 10 µg or 20 µg—each rabbit received four doses of the same injectate. Four rabbits received one injection of the buffer, $TGF\beta_2$ 5 µg, 10 µg or 20 µg. One rabbit received 2 injections of $TGF\beta_2$ 20 ug and one rabbit received 3 injections of 20 ug $TGF\beta_2$. When rabbits received multiple injections, they were separated by 24 hours. All injections had a total volume of 2 ml.

In a dose response study, rabbits received single intrapleural injections of $TGF\beta_2$ 0.167 µg (n=4), 0.50 µg (n=10), 1.67 µg (n=10) or 5 µg (n=12), or the buffer alone (n=5). The total volume of each injection was 2 ml.

The chest tube was left in place for 96 hours following the initial pleural injection or until the volume of pleural fluid aspirated was less than 3 ml. Attempts were made to aspirate all fluid from the pleural space daily after the initial pleural injection. The total volume of aspirated pleural fluid was recorded. In the pilot study if an animal was scheduled to have an additional intrapleural instillation, the aspiration was performed immediately before the instillation. The levels of glucose, protein, and lactic dehydrogenase (LDH) were determined using a Vitros Model 950 automated analyzer (Johnson & Johnson, Rochester, N.Y.). The white cell count was performed with a hemocytometer. Leukocyte differentials were determined by manually counting 100 cells on a Wright's- stained smear.

Rabbits were sacrificed at 14 days by the intravenous injection of pentobarbital. The thorax was removed in block. The trachea was intubated with a small silastic catheter and the lungs were inflated with 10% formalin. After the inflation, the trachea was ligated with plastic ties and the entire thorax was submerged in 10% formalin solution for at least 48 hours.

The necropsy was performed by two of the investigators who were blinded as to the treatment. Each pleural cavity was exposed by making bilateral incisions through the diaphragms, and through all the ribs in approximately the midclavicular line. In this manner, the sternum and the medial portions of the anterior ribs were removed so that the lung and pleural cavities could be evaluated. The presence or absence of hemothorax (clotted blood in the pleural cavity ) and the position of the mediastinum in each animal were recorded.

The degree of pleurodesis observed grossly was graded according to the following scheme:
0—normal pleural space;
1—1 to 3 small adhesions in the pleural space;
2—>3 scattered adhesions but the lung easily separates from the chest wall;
3-generalized scattered adhesions with areas where the lung can be separated from the chest wall only with difficulty;
4—complete obliteration of the pleural space by adhesion.

The degree of pleurodesis and the characteristics of the pleural fluid after the administration of 5 ug TGF were compared to results obtained after the intrapleural administration of 400 mg talc or 10 mg doxycycline which have been reported previously (41). The protocol that had been followed in the rabbits that had been given doxycycline and talc was essentially identical to that which was used for the single-dose TGF injections.

Statistical Analysis

All data are expressed as the mean±standard error of the mean unless otherwise stated. The pleurodesis scores and pleural fluid volume, LDH, white blood cell counts and differential cell counts in the different groups were compared using two way repeated measures analysis of variance. The means in the various groups were compared using the Student-Newman-Keuls Mthoda.Tukey Test. If the data failed tests of normality or equal variance, the medians were compared using the Kruskal-Wallis One Way Analysis of Variance on Ranks. The medians were compared using Dunn's method (Sigma Stat, Jandel Scientific, San Raphael, Calif.). Differences in the results were considered significant when $p<0.05$.

Specific findings of the first experiment demonstrated that the intrapleural injection of $TGF\beta_2$ could produce a pleurodesis (Table 3). All rabbits that received $TGF\beta_2$ intrapleurally had a pleurodesis score of 4. In contrast, the two rabbits that received one or four injections of the buffer alone had pleurodesis scores of only 0 and 1. In addition, the pilot study showed that a single injection of $TGF\beta_2$ at a dose of 5, 10 or 20 µg could produce a pleurodesis. The fibrous reaction with the higher doses was actually more than would be ideal in producing a pleurodesis. All the rabbits except the one that received a single dose of 5 µg had some adhesions in the contralateral pleural space. The rabbit that received 4 separate doses of 20 µg $TGF\beta_2$ had fibrin balls in the peritoneal cavity, 112 ml of straw colored peritoneal fluid, 28 ml bloody pleural fluid in the right pleural space and a pleurodesis score of 3 on the left (control) side. The rabbit that received three separate doses of 20 µg $TGF\beta_2$ had similar findings but had no fibrin balls in the peritoneal cavity. The rabbit that received 4 separate doses of 10 µg $TGF\beta_2$ had no fibrin balls in the peritoneal cavity but did have 100 ml of straw colored peritoneal fluid, 8 ml of pleural fluid and a pleurodesis score of 2 on the control side. The rabbit that received a single dose of 5 µg $TGF\beta_2$ had no pleural or peritoneal fluid and had a pleurodesis score of 0 on the control side.

In the first study, the intrapleural injection of $TGF\beta_2$ resulted in the formation of large amounts of pleural fluid which was characterized by a relatively low WBC and LDH levels (Table 1). Several of the rabbits had more than 20 ml pleural fluid present at the 24 hour time period.

time the mean pleural fluid LDH levels after the intrapleural injections of $TGF\beta_2$, talc and doxycycline were 2,965, 26,435 and 29,593, IU, respectively.

TABLE 1

| Rabbit | Dose | # Inject | Score | | Volume | | | | WBC | | | LDH | | | Protein | | |
|---|---|---|---|---|---|---|---|---|---|---|---|---|---|---|---|---|---|
| | | | Right | Left | 24 h | 38 h | 72 j | Total | 24 h | 48 h | 72 h | 24 h | 48 h | 72 h | 24 h | 48 h | 72 h |
| 277 | control | 1 | 0 | 0 | 3.5 | 2 | 5 | 18.5 | 34362 | 16094 | 5871 | 6023 | 4177 | 3496 | 3.6 | 3.6 | 3.2 |
| 286 | control | 4 | 1 | 1 | 3 | 2 | 5 | 19.3 | 10156 | 4167 | 7767 | 13601 | 4821 | 1719 | 2 | 2.9 | 3.3 |
| 280 | 5 μg | 1 | 4 | 0 | 0 | 7 | 16 | 54.5 | | 742 | 1013 | | 1622 | 3072 | | 3.2 | 3.5 |
| 282 | 5 μg | 4 | 4 | 2 | 24 | 24 | 4 | 81.5 | 915 | 350 | 127 | 1799 | 382 | 524 | 3.4 | 2.8 | 2.8 |
| 278 | 10 μg | 1 | 4 | 2 | 35 | 22 | 10 | 78 | 1467 | 613 | 1346 | 4665 | 1654 | 877 | 3.1 | 3.1 | 3.3 |
| 281 | 10 μg | 4 | 4 | 2 | 11 | 30 | 26 | 120 | 975 | 379 | 684 | 7232 | 1629 | 880 | 3.1 | 2.1 | 2.2 |
| 279 | 20 μg | 1 | 4 | 2 | 24 | 15 | 17 | 70 | 1376 | 492 | 517 | 4620 | 1003 | 865 | 3.3 | 3.2 | 3.5 |
| 285 | 20 μg | 2 | 4 | 2 | 22 | 40 | 10 | 107 | 1508 | 492 | 661 | 4500 | 484 | 853 | 2.1 | 2.5 | 3.1 |
| 284 | 20 μg | 3 | 4 | 3 | 15 | 28 | 22 | 131 | 1377 | 488 | 385 | 7843 | 783 | 688 | 3 | 3 | 3.1 |
| 283 | 20 μg | 4 | 4 | 3 | 17 | 25 | 18 | 122 | 1147 | 506 | 392 | 1342 | 404 | 589 | 3.1 | 2.1 | 2 |

In the dose-response study, single intrapleural injections of $TGF\beta_2$ resulted in pleurodesis in a dose-dependent manner (FIG. 1). The mean pleurodesis score in the group that received 5 μg $TGF\beta_2$ (3.6±0.9) was significantly higher than the mean pleurodesis score in the groups that received 1.67 μg (2.6±1.4, p=0.045), 0.50 μg (1.5±1.0, p<0.001), 0.167 μg (0.6±0.9, p<0.001) or the buffer (0.3±0.1, p<0.001). The mean score for the group that received 1.67 μg was significantly greater than that for the group that received 0.50 μg (p=0.012), 0.167 μg (p=0.003) or the buffer solution (p<0.001). In none of the rabbits did the mean degree of pleurodesis on the left (control) side exceed 1. Since the pleurodesis scores were very low and did not differ significantly in the control and 0.167 μg groups, these groups were combined for statistical analysis of the pleural fluid results.

Figure 2:
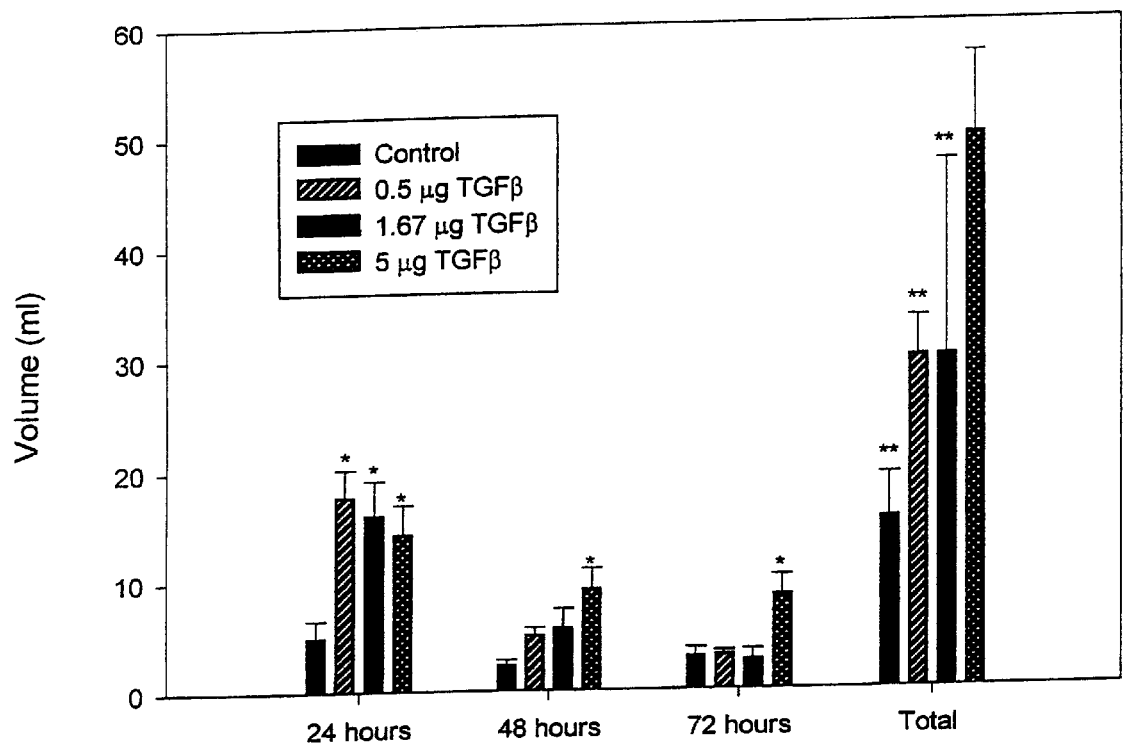
FIG. 2. Mean amount of pleural fluid produced during each of the first three days and the total amount of fluid produced (including at autopsy) after the intrapleural injection of various amounts of TGFβ$_2$, the buffer alone, doxycycline or talc. Note that there is much more fluid after the intrapleural injection of TGF $β_2$.

The intrapleural injection of $TGF\beta_2$ resulted in a high volume pleural effusion (FIG. 2). The fluid collected at 24 hours was an exudate in that the mean pleural fluid LDH exceeded 2000 IU (FIG. 3), although the mean protein levels at 24 hours were in the 2.7–3.0 gm/dl range. The amount of pleural fluid was significantly (p<0.02) greater in the groups that received the three higher doses of $TGF\beta_2$ than it was in the control group at 24 hours. The group that received 5 μg $TGF\beta_2$ had significantly higher fluid volumes at 48 and 72 hours. When the total amount of fluid (including that obtained at autopsy) was compared, the mean amount of fluid was significantly more in the rabbits that received 5 μg $TGF\beta_2$ than in all the other groups (p<0.05).

Figure 3:
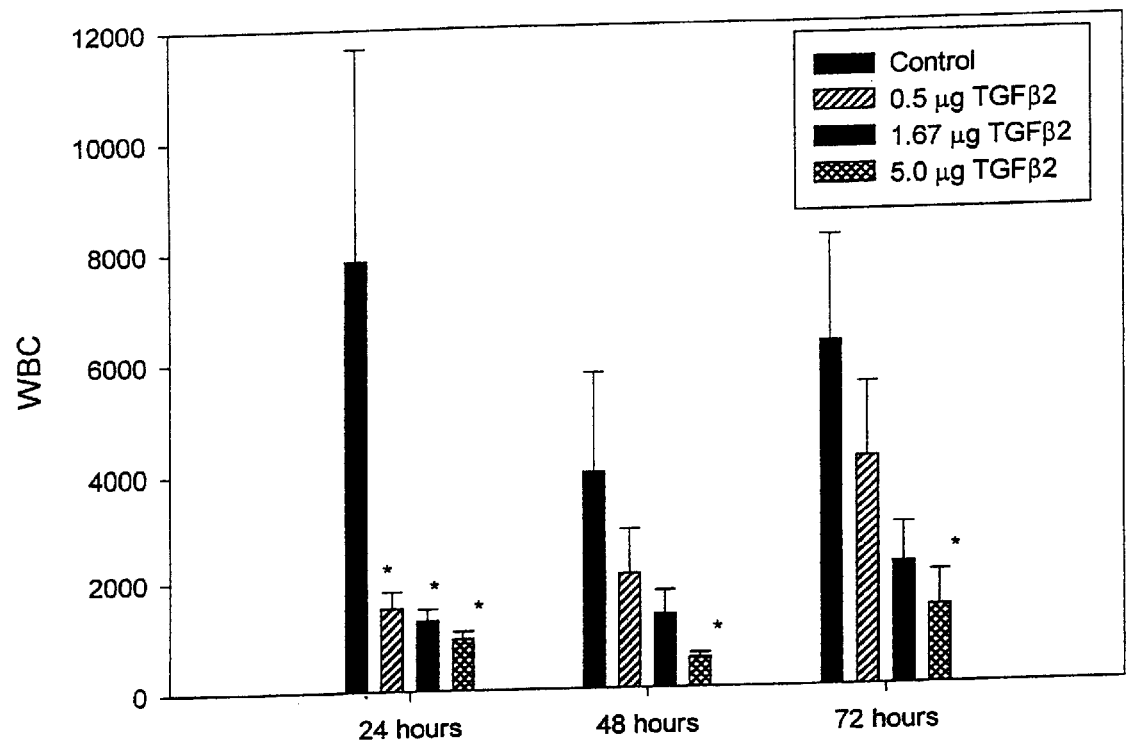
FIG. 3. Mean pleural fluid white blood cell counts on the first three days after the intrapleural injection of various amounts of TGF $β_2$ and buffer alone.
Figure 4:
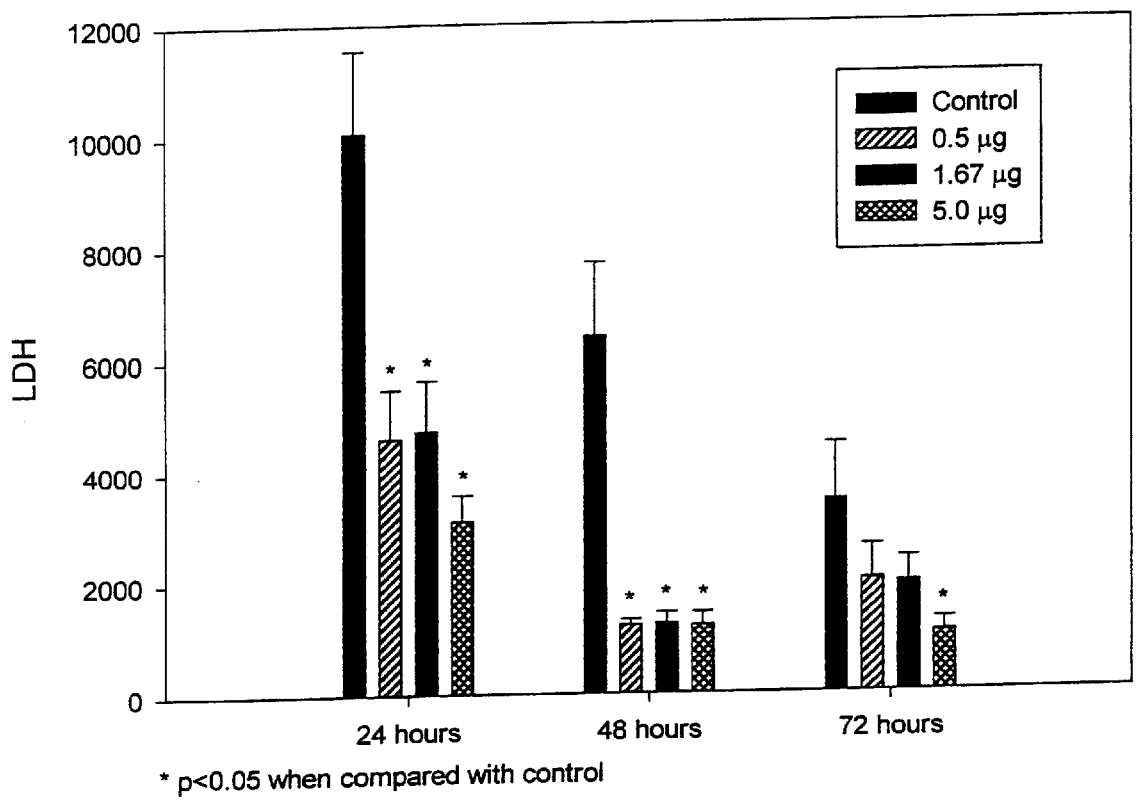
FIG. 4. Mean pleural fluid LDH levels on the first three days after the intrapleural injection of various amounts of TGF β2 and the buffer alone.

Although the intrapleural injection of $TGF\beta_2$ induced the accumulation of a large amount of pleural fluid, the fluid did not appear to be particularly inflammatory (FIGS. 3 and 4). The pleural fluid WBC and LDH level were both significantly lower in the group that received 5 μg $TGF\beta_2$ than they were in the control group on all three days.

Figure 5:
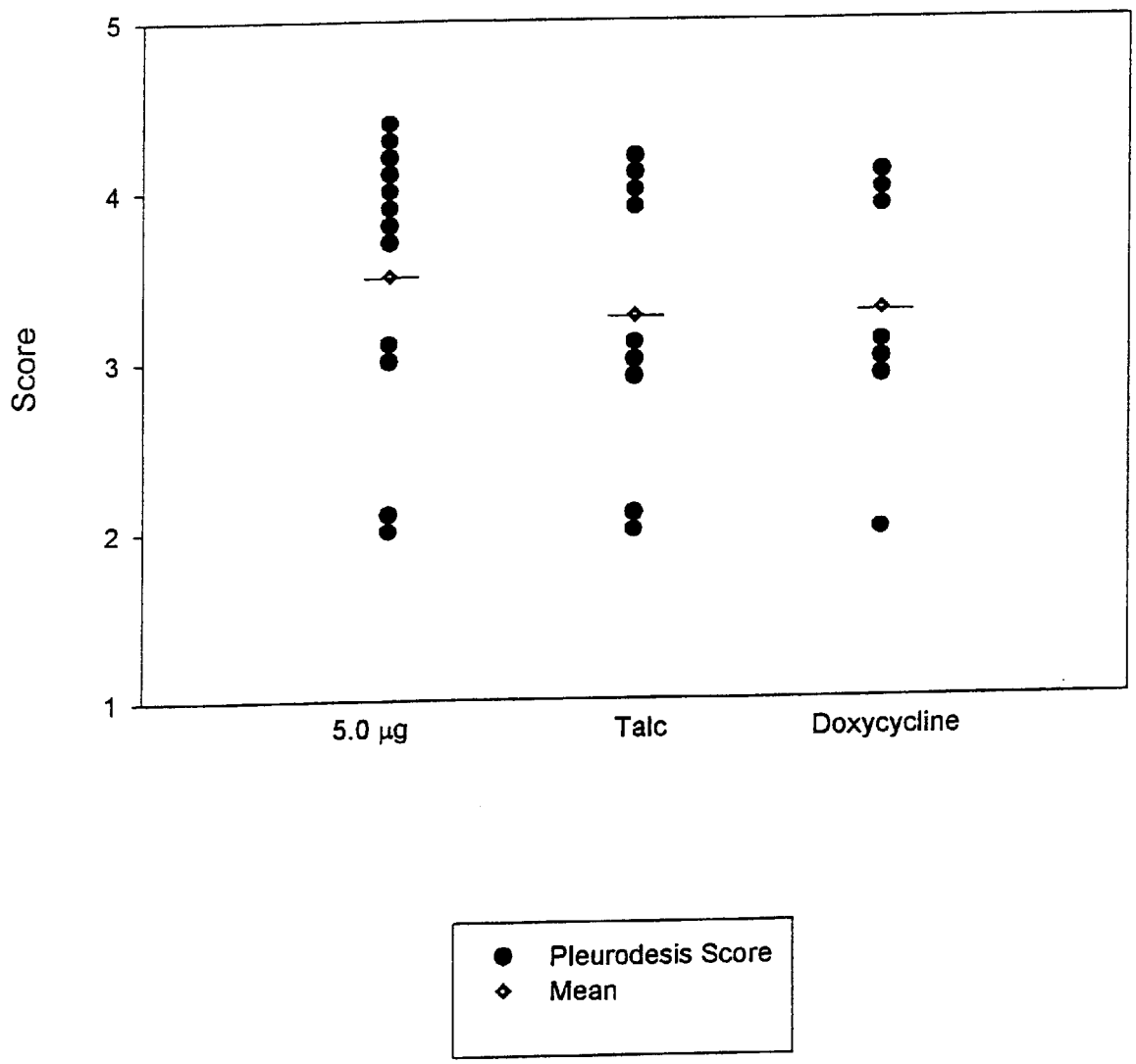
FIG. 5. Mean degree of pleurodesis after the intrapleural injection of TGF β2 (5.0 μg), doxycycline (10 mg/kg) and talc slurry (400 mg/kg).
Figure 6:
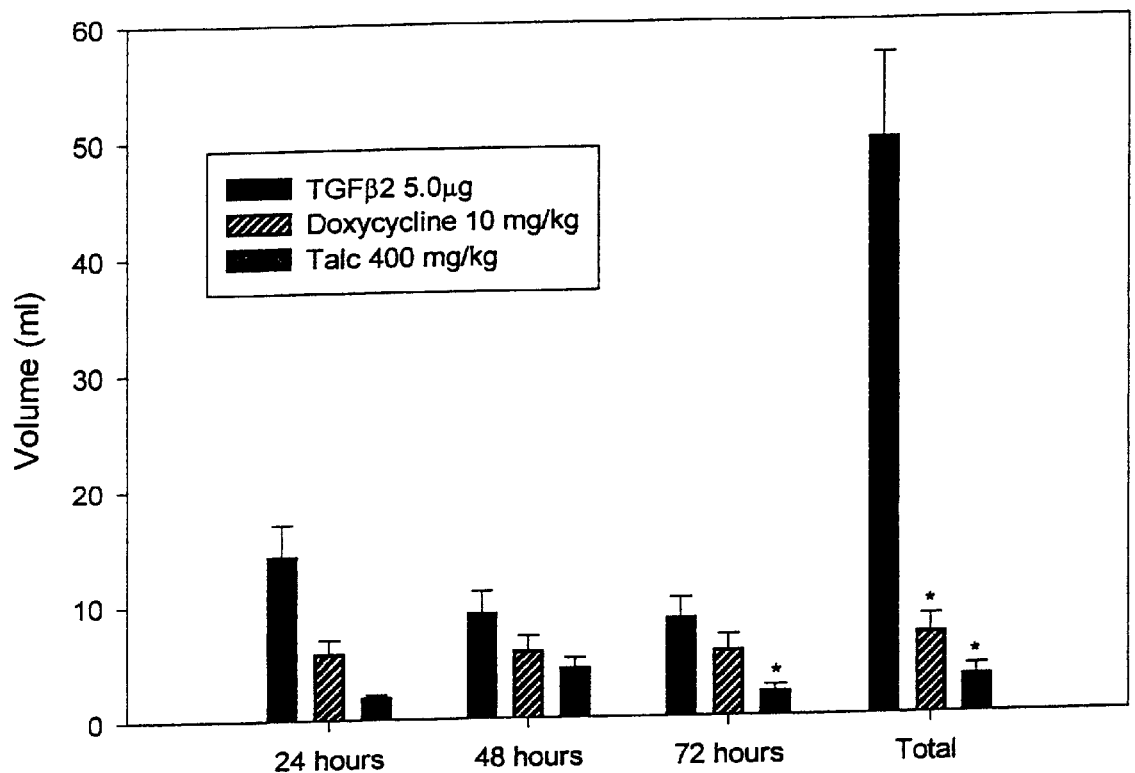
FIG. 6. Mean amount of pleural fluid produced during each of the first three days and the total amount of fluid produced (including at autopsy) after the intrapleural injection of TGF $β_2$ (5 μg), doxycycline (10 mg/kg) or talc slurry (400 mg/kg). Note that there is much more fluid after the intrapleural injection of TGF $β_2$.
Figure 7:
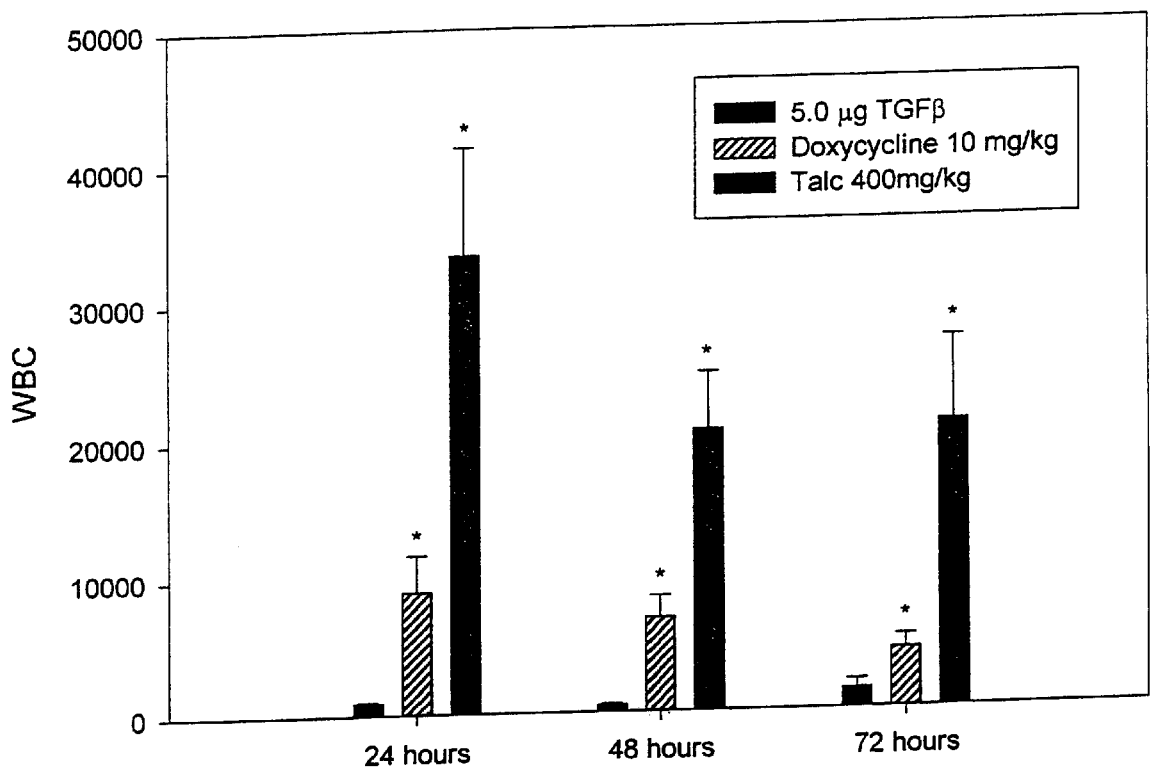
FIG. 7. Mean WBC counts in the pleural fluid during each of the first three days after the intrapleural injection of TGF $β_2$ (5 μg), doxycycline (10 mg/kg) or talc slurry (400 mg/kg).
Figure 8:
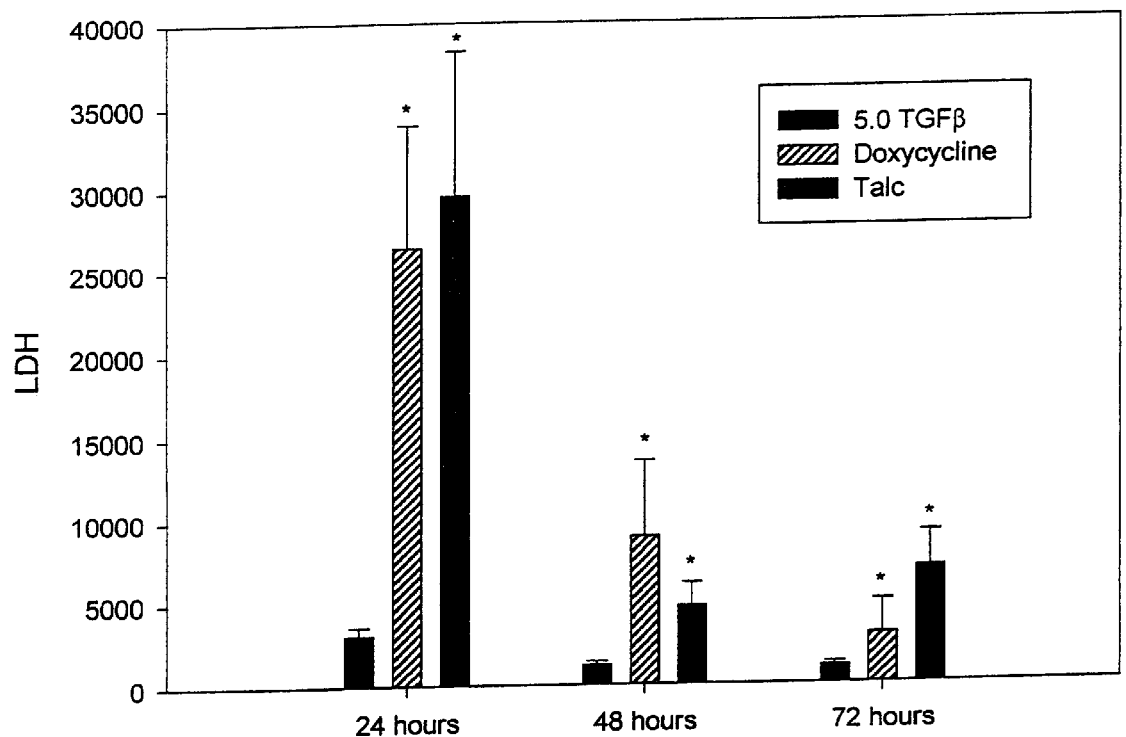
FIG. 8. Mean pleural fluid LDH levels during each of the first three days after the intrapleural injection of TGF $β_2$ (5 μg), doxycycline (10 mg/kg) or talc slurry (400 mg/kg).

The results of the intrapleural injection of 5.0 μg $TGF\beta_2$ were compared with the results of the injection of doxycycline 10 mg/kg or talc slurry 400 mg/kg. Although there were no significant differences in the pleurodesis scores (FIG. 5), the pleural fluid that resulted from the intrapleural injection of doxycycline and talc was much less in volume (FIG. 6) but was more inflammatory than that which resulted from the intrapleural injection of $TGF\beta_2$ (FIGS. 7 and 8). At 24 hours post-injection, the mean pleural fluid WBC after the intrapleural injection of $TGF\beta_2$, talc and doxycycline were 830, 6,430 and 29,149/mm³, respectively. At this same EXAMPLE 3
Production of Pleurodesis in a Sheep Model The present study demonstrates that $TGF\beta$ is effective in producing pleurodesis in sheep—an animal species with a thick pleural membrane similar to that of human. $TGF\beta$ induced pleurodesis in a dose-dependent fashion and was effective in creating symphysis even at the low dose of 0.25 μg/kg. At this dosage, there was no histological evidence of systemic complications in the organs biopsied.

The rabbit is the most common animal model used to study pleurodesis (61, 66, 67) although dogs (61, 62) and pigs (63) have occasionally been studied. The visceral pleurae of small animals (e.g. rabbits, dogs and cats) are thin and different in structure when compared with pleurae of larger animals (e.g. sheep, horses and cows) (58). Pleurae of the latter group are more similar to human pleura which is relatively thick. Results of pleurodesis studies using animals of thin pleura often demonstrated findings different from that in human. For example, bleomycin was completely ineffective in creating pleurodesis in rabbits (65) and a much higher dose of talc is required to produce satisfactory pleurodesis in rabbits (66) than in human. The sheep model serves as a useful method for predicting pleurodesis in humans.

Reagents

A recombinant human $TGF\beta_2$ (Genzyme Corp., Cambridge, Mass., USA) produced in Chinese hamster ovary cells was used. $TGF\beta_2$ was formulated in a vehicle consisting of 20 mM sodium phosphate, 130 mM sodium chloride, 15% (w/w) propylene glycol and 20% (w/w) polyethylene glycol 400. The pH of the solution was 7.2. The vehicle was prepared using USP/NF grade reagents in water for injection and sterile-filtered through a 0.2 micron filter. The $TGF\beta_2$ concentration was determined by a sandwich enzyme-linked immunosorbent assay utilizing two monoclonal antibodies that cross-react with both $TGF\beta_2$ and $TGF\beta_3$. The activity of $TGF\beta_2$ was determined using a mink lung cell (Mv1Lu) antiproliferation assay, modified from the method described by Ogawa (57).

Animal Model

To determine the dose response relationship of $TGF\beta$-induced pleurodesis in sheep, twelve yearling sheep of mixed breeds (24–35 kg) were divided into four groups. A single intrapleural injection of $TGF\beta_2$ at 1.0 (Group A), 0.50 (Group B), 0.25 (Group C) and 0.125 (Group D) μg/kg was administered to each of the four groups. These doses wer e chosen based on results of a pilot study in which sheep receiving 2 μg/kg of TGFμ$_2$ developed complete pleural symphysis.

The sheep was anesthetized with an intravenous injection of 2.5% sodium thiopental (Abbott, North Chicago, Ill., USA) at 20 mg/kg. After the chest was shaven, the sheep was placed in the lateral decubitus position. The skin was sterilized with 2% chlorhexadine (DVM, Miami, Fla., USA) and then with 10% povidone iodine (Baxter, Deerfield, Ill., USA). A 5cm incision was made in the right lateral chest wall at the 7$^{th}$ intercostal space. By blunt dissection, a 18G French Foley ballooned-catheter with 30 mL balloon volume (Bard, Covington, Ga., USA) was inserted into the pleural space under aseptic conditions and secured at the muscle layers and the skin with purse string sutures. The sheep was then ventilated with a positive end expiratory pressure of 15 cmH$_2$O. A three-way stopcock was attached to the end of the Foley catheter through which all air was evacuated from the pleural space immediately after the chest tube insertion.

All sheep received a chest tube in the right pleural space through which TGFβ$_2$ was administered as a single intrapleural injection twenty-four hours after its insertion. The volume of injection was standardized at 1.0 mL/kg. The sheep in Groups C and D also received a chest tube in the left pleural space through which an equal volume of the buffer was injected to serve as the control.

On subsequent days the chest tube was aspirated (with the Foley catheter balloon inflated) for any pleural fluid produced. The volume of the fluid was recorded. Total leukocyte count was measured using an automated counter (Coulter Electronics, Luton, England) which was calibrated daily. The first reading was discarded and the mean of the next three readings was recorded. The protein, glucose and lactate dehydrogenase (LDH) levels were determined with a Vitros Model 950 automated analyzer (Johnson & Johnson, Rochester, N.Y., USA). The chest tube was removed when the pleural fluid drainage was less than 10 ml per day on two consecutive days.

Fourteen days after the intrapleural injection of TGFβ$_2$, the sheep were sacrificed with an injection of 10 ml of Henry Schein Pharmaceuticals Euthanasia Solution 5, comprising pentobarbital 5 gm/ml. At the time of sacrifice, a consensus grading was reached on the degree of pleurodesis and the extent of any hemothorax using a semi-quantitative scheme (as below) by two investigators who were blinded to the treatment. Any evidence of infection or empyema were also inspected for and recorded if present. To assess for any systemic effect of the intrapleural administration of TGFβ$_2$, macroscopic examination and biopsies were performed on the ipsilateral and contralateral pleura and lungs, the pericardium, liver, spleen, diaphragm, kidneys, adrenals, ureter, urinary bladder, omentum, the small intestine and (in female sheep) the ovaries and fallopian tubes.

Pleurodesis Scoring Scheme

The degree of pleurodesis was graded on a scale of 1 to 8. Adhesions were defined as fibrous connections between the visceral and parietal pleura. Symphysis was present if the visceral and parietal pleura were difficult to separate as a result of adhesions.

1=No adhesions between the visceral and parietal pleura;
2=Rare adhesions between the visceral and parietal pleura with no symphysis
3=A few scattered adhesions between the visceral and parietal pleura with no symphysis;
4=Many adhesions between the visceral and parietal pleura with no symphysis;
5=Many adhesions between the visceral and parietal pleura with symphysis involving less than 5% of the hemithorax;
6=Many adhesions between the visceral and parietal pleura with symphysis involving 5% to 25% of the hemithorax;
7=Many adhesions between the visceral and parietal pleura with symphysis involving 25% to 50% of the hemithorax;
8=Many adhesions between the visceral and parietal pleura with symphysis involving greater than 50% of the hemithorax;

The extent of hemothorax was graded 0 to 4.
0=no evidence of hemothorax
1=hemothorax involving<15% of the hemithorax
2=hemothorax involving 15–33% of the hemithorax
3=hemothorax involving 33–75% of the hemithorax
4=hemothorax involving>75% of the hemithorax Infection and Empyema were graded as present or absent.

Statistical Analysis

One Way Analysis of Variance was used to compare the values among subgroups and Tukey Test was used to perform multiple comparison procedures. A p value of less than 0.05 was considered significant. All data were analyzed with Sigma Stat V3.0 statistic software program (Jandel Scientific; San Rafael, Calif., U.S.A.).

Pleurodesis

The intrapleural injection of TGFβ was very effective in inducing pleurodesis. The intrapleural TGFβ at 1.0 μg/kg, 0.5 μg/kg and 0.25 μg/kg (Groups A, B and C) produced a maximum pleurodesis score of 8 in all nine sheep receiving these doses. The three sheep receiving 0.125 μg/kg (Group D) all had a pleurodesis score of 6. At the time of sacrifice, the lungs in all these sheep were tightly adhered to the chest wall and not easily separable. The lung could only be removed from the chest after intense blunt dissection. Nevertheless, after the lung was freed from the chest wall, it could be easily inflated with positive pressure.

In the six sheep (Groups C and D) that had buffer injection into the left (control) pleural space, there was essentially no pleurodesis with scores 1 to 2 in all the animals. One sheep (Group D) had evidence of a small loculated empyema in the left pleural space (control side) at the post-mortem examination. There was no hemothorax in any of the sheep.

Figure 9:
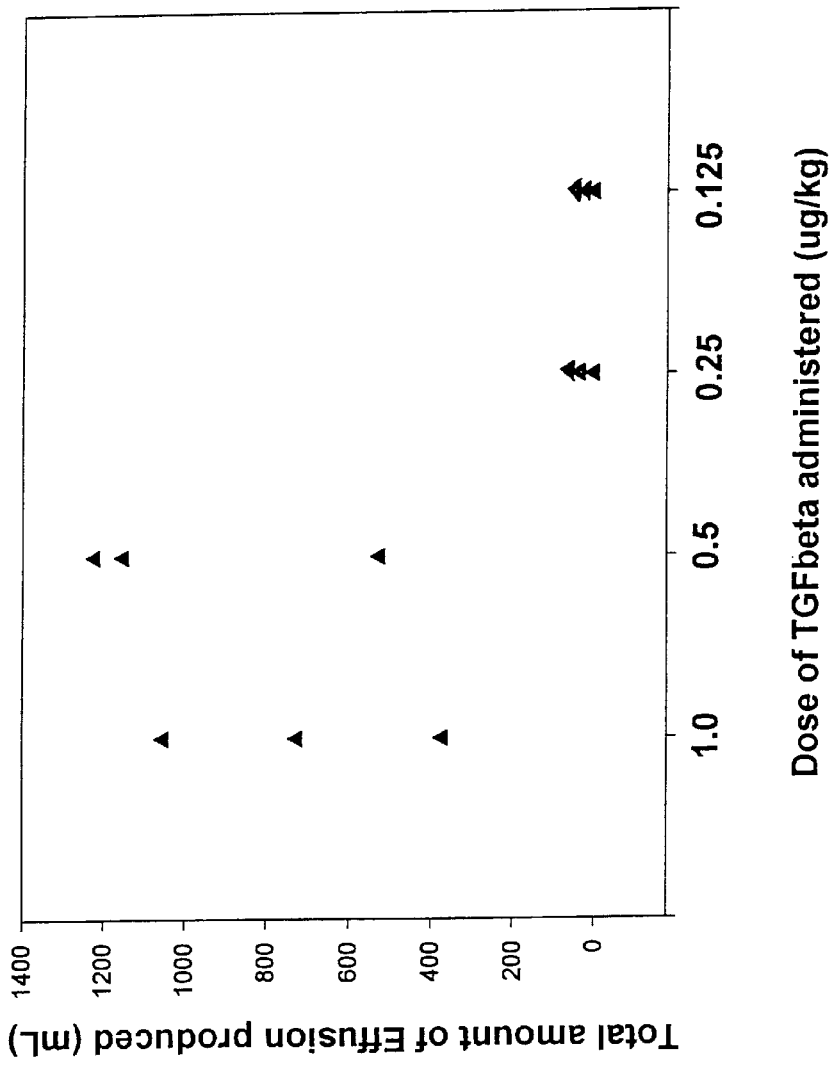
FIG. 9. Volume of total pleural effusion following intrapleural injection of TGF beta. The total effusate for each sheep in the study is denoted by a closed triangle symbol. The grouping represents the dose of TGF beta administered in descending amount from left to right.

The volume of effusion produced at 24 hours and in total, the biochemical analysis and the total leukocyte count of the pleural fluid from the treatment side from each individual sheep (Table 2) and in each dosage group (Table 3) were summarized. The comparison of the total volume of effusion is shown in FIG. 9.

All six sheep receiving 0.125 and 0.25 μg/kg (Groups C and D) had no significant (<5mL) pleural fluid production while sheep receiving higher doses produced large volume of effusion after TGF intrapleural administration. Of the remaining six sheep receiving either 0.5 or 1.0 μg/kg (Groups A and B), there were no significant drainage after 72 hours. None of the sheep developed more than 2 mL of effusion on the control side. The volume was considered insignificant and the fluid was not analyzed. The effusions produced were exudative with mean protein concentrations of 3.9 mg/dL in Group A and 3.6 mg/dL in Group B and mean LDH levels of 958 IU and 896 IU respectively. The white cell counts were relatively low but increased with decreasing dose of TGFβ$_2$ (1352 in Group A, 1938 Group B and 3475 in Group C), although the difference did not reach statistical significance (p=0.11).

TABLE 2

Summary Of Results In All Sheep Studied

| Sheep | Dose (µg/kg) | Pleurodesis Score | Effusion Volume at 24 Hours (mL) | Total Volume of Effusion (mL) | Leukocyte Count (/mm$^3$) | Protein (mg/dL) | LDH (IU) | Glucose (mg/dL) |
|---|---|---|---|---|---|---|---|---|
| 1 | 1.0 | 8 | 720 | 723 | 1544 | 4.1 | 977 | 77 |
| 2 | 1.0 | 8 | 30 | 370 | 217 | 3.8 | 870 | 75 |
| 3 | 1.0 | 8 | 1050 | 1051 | 2295 | 3.8 | 1026 | 66 |
| 4 | 0.5 | 8 | 740 | 1150 | 877 | 3.4 | 1048 | 62 |
| 5 | 0.5 | 8 | 690 | 1210 | 2648 | 4.0 | 904 | 63 |
| 6 | 0.5 | 8 | 500 | 525 | 2288 | 3.5 | 736 | 61 |
| 7 | 0.25 | 8 | 1 | 1 | 3552 | # | # | # |
| 8 | 0.25 | 8 | 1 | 1 | 3399 | # | # | # |
| 9 | 0.25 | 8 | 0 | 0 | # | # | # | # |
| 10 | 0.125 | 6 | 0 | 0 | # | # | # | # |
| 11 | 0.125 | 6 | 0 | 0 | # | # | # | # |
| 12 | 0.125 | 6 | 0 | 0 | # | # | # | # |

All biochemical and hematological values were given for the pleural fluid sample at 24 hours after TGFβ$_2$ administration.
# = Insufficient fluid for analysis.

TABLE 3

Results of Pleurodesis Score, Volume of Effusion produced and Analysis of Pleural Effusion in Sheep after intrapleural TGFβ administration.

| Groups | A | B | C | D |
|---|---|---|---|---|
| TGFβ Dose (µg/kg) | 1.0 | 0.5 | 0.25 | 0.125 |
| No. of Sheep | 3 | 3 | 3 | 3 |
| Pleurodesis Score (1–8) | 8 | 8 | 8 | 6 |
| Effusion Volume at 24 Hour (mL) | 600.0 ± 520.5 | 643.3 ± 126.6 | 0.3 ± 0.6 | 0.0 ± 0.0 |
| Total Effusion Volume (mL) | 714.7 ± 340.6 | 965.0 ± 382.7 | 0.7 ± 0.6 | 0.0 ± 0.0 |
| Protein (mg/dL) | 3.9 ± 0.2 | 3.6 ± 0.3 | # | # |
| LDH (IU) | 958 ± 80 | 896 ± 156 | # | # |
| Glucose (mg/dL) | 72.7 ± 5.9 | 62.0 ± 1.0 | # | # |
| WBC (/mm$^3$) | 1352 ± 1052 | 1938 ± 936 | 3475 ± 108 | # |

# = Insufficient fluid for analysis

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

References

1. Ught R W, Vargas F S; Pleural sclerosis for the treatment of pneumothorax and pleural effusion. Lung 1997; 175:213–223.
2. Light R K O'Hara V S, Maditz T E, McEhinney A J, Butz R, Haakenson C M, Read R C, Sassoon C S, Eastridge C E, Berger R, Fontenelle U, Bell R H, Jenkinson S G, Shure D, Merrill W, Hoover E, Campbell S C: Intrapleural tetracycline for the prevention of recurrent spontaneous pneumothorax, JAMA 1990; 264:2224–2230.
3. Milanez Campos J R, Werebe E C. Vargas F S, Jatene F B, Light R W: Respiratory failure due to insufflated talc. Lancet 1997; 349:251–252.
4. Vargas F S, Wang N-S, Lee H M, Gruer S E, Sassoon C S H, Light R W: Effectiveness of bleomycin In comparison to tetracycline as pleural sclerosing agent in rabbits. Chest 1993; 1041582–1584.
5. Ariel I M, Ornpeza R, Pack G T: Intracavitary administration of radio2otive isotopes in the control of effusions due to cancer. Cancer 1965; 19:1096–1101.
6. Weisberger A S, Bonte F J, Suhrland L G. Management of malignant serous effusions. Geriatrics 1956; 11:23–30.
7. Austin E H, Flye M W: The treatment of recurrent malignant pleural effusion. Ann Thorac Surg 1979. 28:190–203.
8. Izblcki R, Waybing B T. Baker L, et al.: Pleural effusion in cancer patients—a prospective randomized study of pleural drainage with the addition of radio-active phosphorous to the pleural space vs—pleural drainage alone, Cancer 1975; 36-,1511–1518.
9. Xie C. Teixeira L R, Wang N-S, McGovern 413, Light R W: Serial observations after high dose talc slurry in the rabbit model for pleurodesis, Lung 1998; 176:299–307.
10. Wu W, Tebceira L R. Light R W: Doxycycline pleurodesis in rabbits. Comparison of results with and without chest tube. Chest 1998; 114–563–568.
11. Sahn S A, Good J T: The effect of common sclerosing agents on the rabbit pleural space, Am Rev Respir Dis 1981; 124:65–67
12. Vargas F S, Teixeira L R, Antonangelo 1, Silva L M M F, Strunz C M C, Light R W, Acute and chronic pleural changes after the intrapleural instillation of mitoxantrone in rabbits. Lung 1998; 176:227–236
13. Kennedy L, Harley R A, Sahn S A, Strange C: Talc slurry pleurodesis, Pleural fluid and histologic analysis Chest 1995; 107,1707–1712.
14. Light R W, Wang N S, Sassoon S C H. Gruer S E, Vargas F S, Comparison of the effectiveness of tetracycline and minocycline as pleural sclerosing agents-Im rabbits. Chest 1W; 106:577–582.
15. Sassoon C S H, Light R W, Vargas F S, Gruer S E, Wang N-S: Temporal evolution of pleural fibrosis induced by 15. intrapleural minocycline injection. Arm J. Respir Crit Care Mad 1995; 151:791–794.
16. Xie C, Teixeira L R, McGovern J P, Light R W: Systemic corticosteroids decrease the effectiveness of talc pleurodesis, Am J. Respir Crit Care Mod 1998; 157:1441–1444.
17. Rogers J T, Chang D-S, Wheeler A, Teixeira L R, Light R W; The effects of tumor necrosis factor alpha (tnfa) blocking antibody on pleurodesis in rabbits, Chest 1998, 114: (to be published)
18. Teixeira L R, Wu W, Light R W: The effect of corticosteroids on pleurodesis induced with doxycycline in rabbits. *Chest* 199T; 112:1378.
19. Lane K, Chang D-S, Rogers J, Blackwell T, Davidson J, LIght R W* An innovative method by pleurodesis can be produced In rabbits. Chest 1998; 114: (to be published)
20. Samad F, Pandey M, Loskutaff D J: Tissue factor gene expression in the adipose tissue of obese mice. PNAS 1998, 95 (13).,7591–7596.
21. Vrans J A, Stang M T, Grande J P, Getz M J: Expression of tissue factor in tumor stroma correlates with progression to invasive human breast cancer paracrine regulation by carcinoma cell-derived members of the transf6rming growth factor beta family, Can Res 1996; 66 (21). 5063–5070
22. Strange C, Baumann M H, Sohn $A, Idell S: Effects of intrapleural heparin or urokinase on the extent of tetracycline-induced pleural disease. Am J. Respir Crit Care Mad 1995; 151:508–515.
23. Rodriguez-Panadero F, Segado A, Martin Juan J, Ayerbe R, Torres Garcia 1, Castillo J: Failure of talc pleurodesis. is associated with increased pleural fibrinolysis. Am J. Respir Crit Care Mad 1995; 151:785–790.
24. Cheng T, Shen H, Giokas D. Gere J, Tenen D G, Scadden D T: Temporal mapping of gene expression levels during the differentiation of individual primary hematopoietic cells. PNAS 1996, 93(23): 13158–13163.
25. Memotani E, Watanabe S, Yoshihara K Arnano K: The effect of oligosaccharides on the production of tumor necrosis factor-alpha by macrophage-like cell line J7741JA-4, J. Vet Med Se 1998; 60(4)-. 519.521
26. Amenta P S, Harrison D; Expression and potential role of the extracellular matrix in hepatic ontogenesis: a review, Micros Res & Tech 1997; 39(4): 372–386.
27. Owens M W, Milligan S A, Grisham M B: Inhibition of pleural mesothelial cell collagen synthesis by nitric oxide, Free Rad Sio & Mod 1996; 21(5): 601–607.
28. Walker-Renard, Vaughan L M, Saln S A: Chemical pleurodesis for malignant pleural effusions. Ann Intern Med 1994; 120:56–64.
29. Milanez-Campos J R, Werebe E C, Vargas F S, Jatene F B, Light R W: Respiratory failure due to insufflated talc. Lancet 1997; 349:251–252.
30. Light R W, O'Hara V S, Moritz T E, McElhinney A J, Butz R, Haakenson C M, Read R C, Sassoon C S, Eastridge C E, Berger R, Fontenelle L J, Bell R H, Jenkinson S G, Shure D, Merrill W, Hoover E, Campbell S C: Intrapleural tetracycline for the prevention of recurrent spontaneous pneumothorax. JAMA 1990; 264:2224–2230.
31. Rehse D H, Aye R W, Florence M G. Respiratory failure following talc pleurodesis. Am J. Surg 1999 May;177(5):437–40.
32. Light R W, Vargas F S: Pleural sclerosis for the treatment of pneumothorax and pleural effusion. Lung 1997; 175:213–223.
33. Grande J P: Role of transforming growth factor—in tissue injury and repair. P.S.E.B.M. 1997; 214:27–40.
34. Perkett E A: Role of growth factors in lung repair and diseases. Curr Opin Pediatr 1995;7:242–9
35. Idell S, Zwieb C, Kumar A, Koenig K B, Johnson A R. Pathways of fibrin turnover of human pleural mesothelial cells in vitro. Am J. Respir Cell Mol Biol 1992;7:414–426. (XxI am sure that this is the correct reference)
36. Rodriguez-Panadero F, Segado A, Martin Juan J, Ayerbe R, Torres Garcia I, Castillo J: Failure of talc pleurodesis is associated with increased pleural fibrinolysis. Am J. Respir Crit Care Med 1995; 151:785–790.
37. Xie C, Teixeira L R, Wang N-S, McGovern J P, Light R W: Serial observations after high dose talc slurry in the rabbit model for pleurodesis. Lung 1998; 176:299–307.
38. Light R W, Wang N S, Sassoon C S H, Gruer S E, Vargas F S. Comparison of the effectiveness of tetracycline and minocycline as pleural sclerosing agents in rabbits. Chest 1994:106:577–582.
39. Xie C, Teixeira L R, McGovern J P, Light R W. Systemic corticosteroids decrease the effectiveness of talc pleurodesis. Am J. Respir Crit Care Med 1998;157:1441–1444.
40. Ogawa Y, Seyedin S M: Purification of transforming growth factors beta 1 and beta 2 from bovine bone and cell culture assays. Methods Enzymol 1991; 198:317–327.
41. Rogers J T, Cheng D, Wheeler A, Teixeira L, Light R W: The effects of tumor necrosis factor alpha (TNF) blocking antibody on pleurodesis in rabbits. Chest 1998; 114:260S
42. Wu W, Teixeira L R, Light R W: Doxycycline pleurodesis in rabbits. Comparison of results with and without chest tube. Chest 1998; 114:563–568.
43. Sahn S A, Good J T: The effect of common sclerosing agents on the rabbit pleural space. Am Rev Respir Dis 1981; 124:65–67
44. Vargas F S, Teixeira L R, Antonangelo L, Silva L M M F, Strunz C M C, Light R W: Acute and chronic pleural changes after the intrapleural instillation of mitoxantrone in rabbits. Lung 1998; 176:227–236.
45. Sime P J, Xing Z, Graham F L, Csaky K G, Gauldie J. Adenovector-mediated gene transfer of active transforming growth factor-beta1 induces prolonged severe fibrosis in rat lung. J. Clin Invest 1997;100:768–776.
46. Coker R K, Laurent G J, Shahzeidi S, Lympany P A, du Bois R M, Jeffery P K, McAnulty
47. R J. Transforming growth factors-beta 1, -beta 2, and -beta 3 stimulate fibroblast procollagen production in vitro but are differentially expressed during bleomycin-induced lung fibrosis. Am J. Pathol 1997;150:981–91.
48. Jagirdar J, Lee T C, Reibman J, Gold L I, Aston C, Begin R, Rom W N. Immunohistochemical localization of transforming growth factor beta isoforms in asbestos-related diseases. Environ Health Perspect 1997;105 Suppl 5:1197–1203.
49. Anscher M S, Kong F M, Andrews K, Clough R, Marks L B, Bentel G, Jirtle R L. Plasma transforming growth factor beta1 as a predictor of radiation pneumonitis. Int J. Radiat Oncol Biol Phys 1998;41:1029–35.
50. Awad M R, El-Gamel A, Hasleton P, Turner D M, Sinnott P J, Hutchinson I V: Genotypic variation in the transforming growth factor-beta1 gene: association with transforming growth factor-beta1 production, fibrotic lung disease and graft fibrosis after lung transplantation. Transplantation 1998;66: 1014–20.
51. Gerwin B I, Lechner J F, Reddel R R, Roberts A B, Robbins K C, Gabrielson E W, Harris C C: Comparison of production of transforming growth factor-beta and platelet-derived growth factor by normal human mesothe- 51. (continued) lial cells and mesothelioma cell lines. Cancer Res 1987;47:6180–4

52. Pertovaara L, Kaipainen A, Mustonen T, Orpana A, Ferrara N, Saksela O, Alitalo K: Vascular endothelial growth factor is induced in response to transforming growth factor-beta in fibroblastic and epithelial cells. J. Biol Chem 1994;269:6271–4

53. Berse B, Hunt J A, Diegel R J, Morganelli P, Yeo K, Brown F, Fava R A. Hypoxia augments cytokine (transforming growth factor-beta (TGF-beta) and IL-1)-induced vascular endothelial growth factor secretion by human synovial fibroblasts. Clin Exp Immunol 1999;1 15:176–82.

54. Brown L F, Detmar M, Claffey K, Nagy J A et al. Vascular permeability factor/vascular endothelial growth factors: A multifunctional angiogenic cytokine. EXS 1997; 79:233–269.

55. Collins P O, Connolly D T, Williams T J. Characterization of increase in vascular permeability induced by vascular permeability factor in vivo. Br J. Pharmacol 1993; 109: 195–199.

56. Vargas F S, Wang N-S, Lee H M, Gruer S E, Sassoon C S H, Light R W: Effectiveness of bleomycin in comparison to tetracycline as pleural sclerosing agent in rabbits. Chest 1993; 104:1582–1584.

57. Light R. W. and F. S. Vargas. 1997. Pleural sclerosis for the treatment of pneumothorax and pleural effusion. Lung 175; 213–223.

58. Walker-Renard P. B., L. M. Vaughan, and S. A. Sahn. 1994. Chemical pleurodesis for malignant pleural effusions. Ann Intern Med 120; 56–64.

59. Milanez J. R., E. C. Werebe, and R. W. Light. 1997. Respiratory failure due to insufflated talc. Lancet 349; 251–252.

60. Rehse D. H., R. W. Aye, and M. G. Florence. Respiratory failure following talc pleurodesis. Am J. Surg 1999; 177: 437–440.

61. Kennedy L., R. A. Harley, S. A. Sahn, and C. Strange. 1995. Talc slurry pleurodesis: Pleural fluid and histologic analysis. Chest 107; 1707–1712.

62. Werebe E C, Pazetti R, Milanze de Campos J R, Fernandez P P, Capelozzi V L, Jatene F B, and Vargas F S. 1999. Systemic distribution of talc after intrapleural administration in rats. Chest 115(1):190–193.

63. Light R. W., Cheng D. S., J. Rogers, J. Davidson, and K. B. Lane. 1999. The intrapleural injection of transforming growth factor $\beta_2$ produces a pleurodesis in rabbits. (in writing).

64. Border W. A. and N. A. Noble. 1994. Transforming Growth Factor $\beta$ in tissue fibrosis. New Engl J. Med 331 (19); 1286–1292.

65. Kelly J. 1993. Transforming growth factor-$\beta$. In: Kelley J, ed. Cytokines of the Lung. Marcel Dekker, New York. 101–137.

66. Light R. W., N.-S. Wang, S. C. H. Sassoon, S. E. Gruer, D. Oliver, and F. S. Vargas. 1994. Talc slurry is an effective pleural sclerosant in rabbits. Chest 107; 1702–1706.

67. Xie C., L. R. Teixeira, J. P. McGovern, and R. W. Light. 1998. Systemic corticosteroids decrease the effectiveness of talc pleurodesis. Am J. Respir Crit Care Med 157; 1441–1447.

68. Albertine K. H., J. P. Wiener-Kronish, P. J. Roos, and N. C. Staub. 1982. Structure, blood supply and lymphatic vessels of the sheep's visceral pleura. Am J Anatomy 165: 277–294.

69. Broaddus V. C., J. P. Wiener-Kronish, and N. C. Staub. 1990. Clearance of lung edema into the pleural space of volume-loaded anesthetized sheep. J Appl Physiol 68 (6): 2623–2630.

70. Wiener-Kronish J. P., K. H. Albertine, V. Licko, and N. C. Staub. 1984. Protein egress and entry rates in pleural fluid and plasma in sheep. J. Appl Physiol 56 (2): 459–463.

71. Ogawa Y., and S. M. Seyedin. 1991. Purification of transforming growth factor beta 1 and beta 2 from bovine and cell culture assays. Methods in Enzymology 198; 317–327.

72. Light R. W. Pleural Diseases. Philadelphia: Lea & Febiger, 1990.

73. Keller S. M. 1993. Current and future therapy for malignant pleural effusions. Chest 103; 63S–67S.

74. Colt H. G., V. Russack, Y. Chiu, R. G. Konopka, P. G. Chiles, C. A. Pedersen, and D. Kapelanski. 1997. A comparison of thoracoscopic talc insufflation, slurry and mechanical abrasion pleurodesis. Chest 111 (2); 442–448.

75. Gallagher L. A., S. J. Birchard, and S. E. Weisbrode. 1990. Effects of tetracycline hydrochloride on pleurae in dogs with induced pleural effusion. Am J Vet Res 51 (10): 1682–1687.

76. Cohen R. G., W. W. Shely, S. E. Thompson, J. A. Hagen, C. C. Marboe, T. R. DeMeester, and V. A. Starnes. 1996. Talc pleurodesis: talc slurry versus thoracoscopic talc insufflation in a porcine model. Ann Thorac Surg 62 (4): 1000–1002.

77. Albertine K. H., J. P. Wiener-Kronish, and N. C. Staub. 1984. Anatomical Record 208; 401–409.

78. Vargas F. S., N. S. Wang, H. M. Lee, S. E. Gruer, C. S. Sassoon, and R. W. Light. 1993. Effectiveness of bleomycin in comparison to tetracycline as pleural sclerosing agent in rabbits. Chest 104(5): 1582–1584.

79. Light R. W., N. S. Wang, C. S. Sassoon, S. E. Gruer, and F. S. Vargas. 1995. Talc slurry is an effective pleural sclerosant in rabbits. Chest 107(6): 1702–1706.

80. Ikubo A., T. Morisaki, M. Katano, H. Kitsuki, K. Anan, A. Uchiyama, M. Tanaka, and M. Torisu. 1995. A possible role of TGF-$\beta$ in the formation of malignant effusions. *Clin Immunol Immunopathology* 77(1):27–32.

81. Berse B., J. A. Hunt, R. J. Diegel, P. Morganelli, K. Yeo, F. Brown, and R. A. Fava. 1999. Hypoxia augments cytokine (Transforming growth factor-beta (TGF-beta) and IL-1)-induced vascular endothelial growth factor secretion by human synovial fibroblasts. *Clin Experiment Immunol* 115(1):176–182.

82. Ferrara N, and B. Keyt. 1997. Vascular endothelial growth factor: Basic biology and clinical implications. EXS 79:209–232.

83. Cheng D. S., Y. C. Lee, J. T. Rogers, E. A. Perkett, U. Lappalainen, R. M. Rodriguez, and R. W. Light. Transforming growth factor $\beta$ isoform levels correlate with vascular endothelial growth factor level in pleural effusions. (Submitted)

84. Rodriguez-Panadero and V. B. Antony. 1997. Pleurodesis: State of the art. Eur Resp J. 10(7):1648–54.

85. Beck L. S., L. DeGuzmand, W. P. Lee, Y. Xu, M. W. Siegel, and E. P. Amento. 1993. One systemic administration of transforming growth factor-beta 1 reverses age- or glucocorticoid-impaired would healing. J. Clin Invest 92.

What is claimed is:

1. A method of producing a pleurodesis in a mammal, comprising introducing a therapeutically effective dose of a pharmaceutical composition comprising TGF$\beta$ into the pleural cavity, whereby pleurodesis is produced.

2. The method of claim 1, wherein the mammal is a human.

3. The method of claim 1, wherein the volume of the pharmaceutical composition injected is 1.0 ml/Kg body weight of the mammal.

4. The method of claim 1, wherein the composition comprises TGFβ and a physiologically acceptable buffer.

5. The method of claim 4, wherein the buffer is phosphate buffered saline.

6. The method of claim 1, wherein the introduced composition comprises TGFβ, sodium phosphate, sodium chloride, propylene glycol and polyethylene glycol 400.

7. The method of claim 5, wherein the $TGF\beta_2$ is present in a dose of 0.125 μg/Kg to 1.0 μg/Kg body weight.

8. The method of claim 4, wherein the concentration of sodium phosphate is 2 mM to 100 mM.

9. The method of claim 4, wherein the concentration of sodium chloride is 10 mM to 200 mM.

10. The method of claim 4, wherein the concentration of propylene glycol is 5% to 25% (w/w).

11. The method of claim 4, wherein the concentration of polyethylene glycol 400 is 5% to 30% (w/w).

12. The method of claim 1, wherein the TGFβ is $TGF\beta_2$.

13. The method of claim 1, wherein the TGFβ is $TGF\beta_1$.

14. The method of claim 1, wherein the TGFβ is $TGF\beta_3$.

* * * * *